United States Patent [19]

Ohno

[11] Patent Number: 5,049,076

[45] Date of Patent: Sep. 17, 1991

[54] METHOD OF BONDING METAL TO DENTINE

[75] Inventor: Hiroki Ohno, Ebetsu, Japan

[73] Assignee: Goushi Kaisha Toukuriki Shoten, Tokyo, Japan

[21] Appl. No.: 481,583

[22] Filed: Feb. 20, 1990

Related U.S. Application Data

[62] Division of Ser. No. 367,760, Jun. 19, 1989, abandoned.

[30] Foreign Application Priority Data

Jun. 22, 1988 [JP] Japan .................................. 63-153853

[51] Int. Cl.$^5$ ................................................ A61C 5/00
[52] U.S. Cl. .................................... 433/215; 433/223; 433/222.1; 433/228.1
[58] Field of Search ..................... 433/215, 228.1, 227, 433/226, 222.1, 223, 209

[56] References Cited

U.S. PATENT DOCUMENTS

| | | | |
|---|---|---|---|
| 4,451,639 | 5/1984 | Prasad | 433/222.1 |
| 4,576,789 | 3/1986 | Prasad | 433/222.1 |
| 4,659,384 | 4/1987 | Daigo et al. | 433/228.1 |

*Primary Examiner*—John J. Wilson
*Attorney, Agent, or Firm*—Price, Heneveld, Cooper, DeWitt & Litton

[57] ABSTRACT

A method comprises the steps of applying a gallium alloy in liquid form to the surface of an adherend metallic portion, and forming an alloy layer containing Ga, Sn, In or Zn on the surface of the adherend metallic portion, whereby an excellent adhesive surface having stability and water resistance can be formed on an adherend metallic portion to be contacted to cement or adhesive resin, by a very easy process without the need to use any special apparatus or instruments during the operation of adhesively bonding a resin portion of a denture base to a metallic portion or a dentine to a restorative metallic material such as an inlay, a crown or the like.

20 Claims, No Drawings

METHOD OF BONDING METAL TO DENTINE

This is a divisional of co-pending application Ser. No. 367,760 filed on June 19, 1989 now abandoned.

BACKGROUND OF THE INVENTION

1. Field of the Invention

This invention relates generally to a method of adhesively bonding a resin portion of a denture base to a metallic portion thereof or of adhesively bonding a dentine to a restorative dental material such as an inlay, a crown or the like by using either adhesive resin or dental cement such as glassionomer cement, polycarboxylate cement or the like. More particularly, the invention relates to a method of improving the quality of the surface of an adherend metallic portion so as to impart stable and high adhesive strength to adhesively bonded portions formed by any of the above-described adhesion methods as well as good water resistance to the adherend surfaces of the adhesively bonded portions.

2. Description of the Related Art

In the field of dental treatment, various kinds of adhesives have recently been developed, such as dental cements or adhesive resins of the type which can be used in contact not only with dentine but with metallic portions.

The adhesives of these conventional types commonly exhibit, after adhesion, extremely superior adhesiveness with respect to Co-Cr alloys and Ni-Cr alloys in a dry atmosphere, but the adhesiveness deteriorates to a material extent in an environment in which water is present. In addition, with respect to rare metals, the aforesaid conventional adhesives are not able to yield satisfactory adhesiveness even in a dry atmosphere since the activity of rare metal surfaces is intrinsically low with respect to the above-described cement and adhesive resin.

In order to overcome the disadvantages described above, various metal surface treatments such as sandblasting treatment, 400° C. high-temperature oxidation treatment, acid treatment, treatment utilizing electrodeposition with tin, and treatment utilizing coating with a glass layer (SiOx-C) have been developed, and attempts have been made to reduce them to practice.

However, even if a treatment is employed which comprises, singly or in combination, the aforesaid treatments such as sandblasting treatment, 400° C. high-temperature oxidation treatment and acid treatment, it is impossible to obtain satisfactory adhesive strength and, further, adherend surfaces may naturally peel due to being immersed in water.

As compared with the aforesaid treatments such as sandblasting treatment, 400° C. high-temperature oxidation treatment and acid treatment, a treatment utilizing electrodeposition with tin or coating with a glass layer can bring about superior adhesiveness and better water resistance of the adherend surfaces. However, systems utilizing electrodeposition with tin, which typically comprise an electrodeposition apparatus, an electrodeposition liquid, a masking set and a cleaning liquid, present a number of problems. First, a tin-electrodeposition system of this kind is expensive; second, the operation is complicated; and, third, the electrodeposition liquid (e.g., Sn-100) readily deteriorates due to oxidation.

On the other hand, a treatment based on the coating of a glass layer requires an apparatus for depositing SiOx-C on the surface of an alloy and also entails the use of chemical agents such as organic silane, a silane coupling agent, and so on. In addition, this method not only necessitates a very expensive apparatus as in the case of a treatment utilizing electrodeposition with tin, but the period during which such chemical agents can be stored is short and a complicated operation is required.

SUMMARY OF THE INVENTION

It is, therefore, an object of the present invention to provide a method of improving the quality of the surface of an adherend metallic portion so as to impart stable and high adhesive strength to adhesively bonded portions as well as good water resistance to adherend surfaces in the case of adhesively bonding a resin portion of a denture base to a metallic portion thereof or of adhesively bonding a dentine to a restorative dental material such as an inlay, a crown or the like by using either adhesive resin or dental cement such as glassionomer cement, polycarboxylate cement or the like.

To achieve the above object, in accordance with the present invention, there is provided a method of forming an adhesive surface for an adherend object on an adherend metallic surface, comprising the steps of applying a gallium alloy in liquid form to the surface of an adherend metallic portion, and forming a new alloy layer containing Ga, Sn, In or Zn on the surface of the adherend metallic portion, thereby improving the quality of the surface of the adherend metallic portion. In accordance with the present invention, it is possible to realize a method which does not require any special apparatus such as that described above, and which is extremely easy to perform, this method being capable of forming an excellent adherend surface for cement or adhesive resin on the surface of a metallic portion of a denture base or the adherend metallic surface of a metallic restorative dental material.

DESCRIPTION OF THE PREFERRED EMBODIMENT

One embodiment of a method in accordance with the present invention will be described below.

A Ga-Sn alloy in liquid form such as a Ga-Sn alloy having a liquid-phase temperature of 20° C. is stuck to a rod made of pure tin, and the pure-tin rod is rubbed against the surface of an adherend metallic portion (made of, for example, a gold-silver-palladium alloy, a gold alloy, or a silver alloy). In this manner, a new alloy layer containing the Ga-Sn alloy is formed on the surface of the adherend metallic portion.

When the method according to the present invention was applied to an alloy which had heretofore exhibited substantially no adhesiveness with respect to any adhesive resin and the resultant adhesiveness was measured with a tensile test, it was found that the adhesive strength thereof was 450 kgf/cm$^2$ or more in an example in which the method was applied to a gold-silver-palladium alloy. This value matches the adhesive strength of an adhesion sample obtained by adhesively bonding a resin to a Co-Cr alloy and aging the adhesively bonded matter in a dry atmosphere.

In addition, with respect to a gold alloy and a silver alloy, similar adhesive strength was obtained.

Moreover, an adhesive resin was stuck to each of these adherend alloys, and the water resistance of the adhesively bonded surfaces was examined after immersion in water. No peeling was observed between the adhesively bonded surfaces, and the water resistance obtained was found to be excellent. This excellent water resistance is far superior to the water resistance of the adhesive resin with respect to a CO-Cr alloy or a Ni-Cr alloy.

Moreover, the method according to the present invention was applied to adhesion of a gold alloy to polycarboxylate cement. The adhesive strength measured with a tensile test was 130 kgf/cm². This value is ten times the typical value previously reported. (The adhesive strength obtained with glassionomer cement was approximately 100 kgf/cm².)

As another example, a Ga-In alloy or a Ga-Zn alloy in liquid form may be stuck to a pure-tin rod and the pure-tin rod then rubbed against the surface of an adherend metallic portion (made of, for example, a gold-silver-palladium alloy, a gold alloy or a silver alloy). In this example as well, it is possible to bring about results similar to those accomplished with respect to the Ga-Sn alloy in liquid form.

It will be appreciated from the foregoing that the present invention provides the following advantages.
1. The process of improving the quality of a metallic surface is extremely easy.
2. Stable and high adhesive strength can be obtained and, therefore, adhesively bonded surfaces do not deteriorate when immersed in water.
3. No special technical knowledge is required to improve the quality of a metallic surface.
4. The method is inexpensive.
5. A nontoxic and innocuous treatment is made available.
6. No deterioration in the quality of the relevant materials occurs.
7. The process of improving the quality of a metallic surface can be carried out in atmospheric air at a normal temperature. Accordingly, even if a prefixed resin crown which is adhesively bonded to a position in the oral cavity is broken or a restorative metallic material which is adhesively bonded by cement comes away, it is possible to repair the portion in question within the oral cavity.

It is to be noted that the present invention is intended to provide a novel method of improving the surface of an adherend metallic portion so as to form thereon an adherend surface which exhibits excellent adhesiveness with respect to cement or adhesive resin and that the method is characterized by the step of forming an alloy layer which serves to improve the adhesiveness on the surface of an adherend metallic portion. Accordingly, the method of improving surface quality in accordance with the present invention essentially differs from any other surface treatment method utilizing tin plating.

What is claimed is:

1. The method of bonding a metallic element to dentine and dentine type material, the steps which include forming an adherent surface coating of an alloy of gallium on the metallic surface, applying an adhesive to the tooth and by means of the adhesive bonding the metallic element to the dentine material with said coating between the metallic element and the adhesive.

2. The method of bonding a metallic element as described in claim 1 including the additional steps of effecting the bond at temperatures which a dental patient can tolerate.

3. The method of bonding a metallic element as described in claim 2 wherein the coating is an alloy of gallium and indium or zinc in liquid form.

4. The method of bonding a metallic element as described in claim 1 in which the coating is an alloy of gallium and tin.

5. The method of bonding a metallic element as described in claim 1 in which the alloy is applied in liquid form.

6. The method of bonding a metallic element as described in claim 1 in which the coating is an alloy of gallium and indium.

7. The method of bonding a metallic element as described in claim 1 in which the coating is an alloy of gallium and zinc.

8. The method of bonding a metallic element as described in claim 1 in which the coating is an alloy of gallium and indium or tin.

9. The method of bonding a metallic element as described in claim 8 wherein the alloy is in liquid form.

10. The method of bonding a metallic element as described in claim 1 wherein said coating is an alloy of gallium and a precious metal.

11. The method of bonding a metallic element as described in claim 10 wherein said precious metal is gold.

12. The method of bonding a metallic element as described in claim 10 wherein said precious is silver.

13. The method of bonding a metallic element as described in claim 10 wherein said precious metal is gold or silver or palladium.

14. In the practice of dentistry the method of bonding a metallic restorative to a tooth which restorative has a metallic surface where it is to be bonded to the tooth, the steps which include forming an adherent surface coating of an alloy of gallium on the metallic surface, applying an adhesive to the tooth and, by means of the adhesive, bonding the dental restorative to the tooth with said coating between the dental restorative and the adhesive.

15. The practice of dentistry as described in claim 14 including the additional steps of effecting the bond at temperatures which a dental patient can tolerate.

16. The practice of dentistry as described in claim 14 in which the coating is an alloy of gallium and tin.

17. The practice of dentistry as described in claim 14 in which the alloy is applied in liquid form.

18. The practice of dentistry as described in claim 14 in which the coating is an alloy of gallium and indium or zinc or tin.

19. The practice of dentistry as described in claim 14 wherein said coating is an alloy of gallium and a precious metal.

20. The practice of dentistry as described in claim 19 wherein said alloy includes gold or silver or palladium.

* * * * *

UNITED STATES PATENT AND TRADEMARK OFFICE
CERTIFICATE OF CORRECTION

PATENT NO. : 5,049,076

DATED : September 17, 1991

INVENTOR(S) : Hiroki Ohno

It is certified that error appears in the above-identified patent and that said Letters Patent is hereby corrected as shown below:

Title page, item [73] Assignee: "Goushi Kaisha Toukuriki Shoten"
should be --Goushi Kaisha Tokuriki Shoten--.
Col. 4
Claim 12, line 2:
after "precious" insert --metal--.

Signed and Sealed this

First Day of June, 1993

Attest:

MICHAEL K. KIRK

Attesting Officer

Acting Commissioner of Patents and Trademarks